United States Patent
Staedler et al.

(10) Patent No.: US 11,124,759 B2
(45) Date of Patent: Sep. 21, 2021

(54) PROCESS FOR BACTERIALLY DEVULCANIZING SULPHUR-VULCANIZED RUBBER PARTICLES

(71) Applicant: TYRE RECYCLING SOLUTIONS SA, Gland (CH)

(72) Inventors: Davide Staedler, Comano (CH); Thibaud Spinetti, Lausanne (CH); Christian Lowe, Commugny (CH)

(73) Assignee: TYRE RECYCLING SOLUTIONS SA, Gland (CH)

( * ) Notice: Subject to any disclaimer, the term of this patent is extended or adjusted under 35 U.S.C. 154(b) by 1255 days.

(21) Appl. No.: 15/326,852

(22) PCT Filed: Jul. 15, 2015

(86) PCT No.: PCT/EP2015/066208
§ 371 (c)(1),
(2) Date: Jan. 17, 2017

(87) PCT Pub. No.: WO2016/008950
PCT Pub. Date: Jan. 21, 2016

(65) Prior Publication Data
US 2017/0211158 A1    Jul. 27, 2017

(30) Foreign Application Priority Data
Jul. 16, 2014  (CH) ...................... 1080/14

(51) Int. Cl.
*C12N 1/20* (2006.01)
*C08J 11/10* (2006.01)
*C12P 5/00* (2006.01)
*C12P 5/02* (2006.01)
*C12R 1/01* (2006.01)

(52) U.S. Cl.
CPC ............. *C12N 1/205* (2021.05); *C08J 11/105* (2013.01); *C12N 1/20* (2013.01); *C12P 5/007* (2013.01); *C12P 5/026* (2013.01); *C08J 2307/00* (2013.01); *C08J 2309/00* (2013.01); *C08J 2309/06* (2013.01); *C08J 2319/00* (2013.01); *C12R 2001/01* (2021.05); *Y02W 30/62* (2015.05)

(58) Field of Classification Search
None
See application file for complete search history.

(56) References Cited

U.S. PATENT DOCUMENTS

| | | | |
|---|---|---|---|
| 5,115,983 A | 5/1992 | Rutherford, Sr. | |
| 7,851,177 B2 * | 12/2010 | Viedma | C12Q 1/04 435/30 |
| 9,441,099 B2 * | 9/2016 | Rakhman | C08L 19/003 |

OTHER PUBLICATIONS

Christiansson et al. "Reduction of surface sulphur upon microbial devulcanization of rubber materials". Biotechnology Letters. 1998, vol. 20, No. 7, pp. 637-642.*
Kelly et al. International Journal of Systematic and Evolutionary Microbiology, 2000, 50, 511-516.*
Medium 36 Thiobacillus medium. DSMZ or DSM Catalogue. 2015, p. 1.*
Romine et al. "Rubbercycle: a bioprocess for surface modification of waste tyre rubber," vol. 59, no. 1-3, 1998, pp. 353-358.
Li et al. "Microbial desulfurization of ground tier rubber by Thiobacillus Ferrooxidans," Polymer Degradation and Stability vol. 96, No. 9, (2011) 1662-1668.
Oct. 19, 2015 Search Report issued in International Patent Application No. PCT/EP2015/066208.

* cited by examiner

*Primary Examiner* — Vera Afremova
(74) *Attorney, Agent, or Firm* — Oliff PLC

(57) ABSTRACT

A new *Acidithiobacillus ferrooxidans* strain as well as a process for bacterially devulcanizing sulphur-vulcanized rubber particles and devulcanized rubber particles obtainable by the process.

14 Claims, 5 Drawing Sheets

FIG: 1
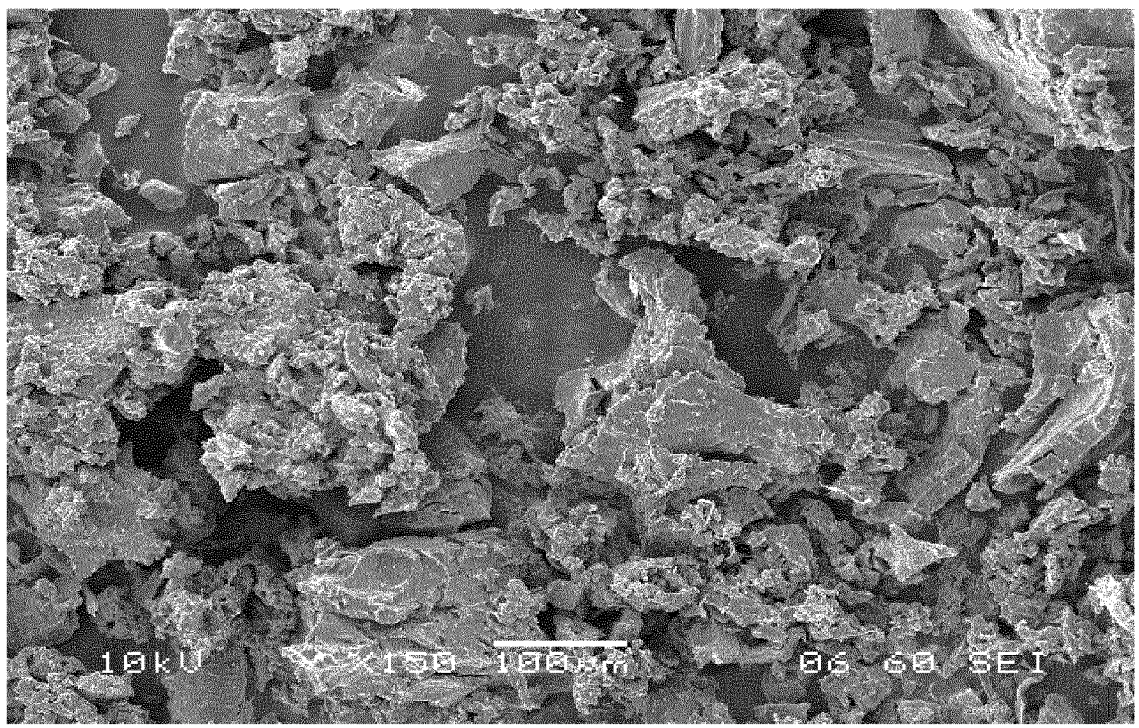
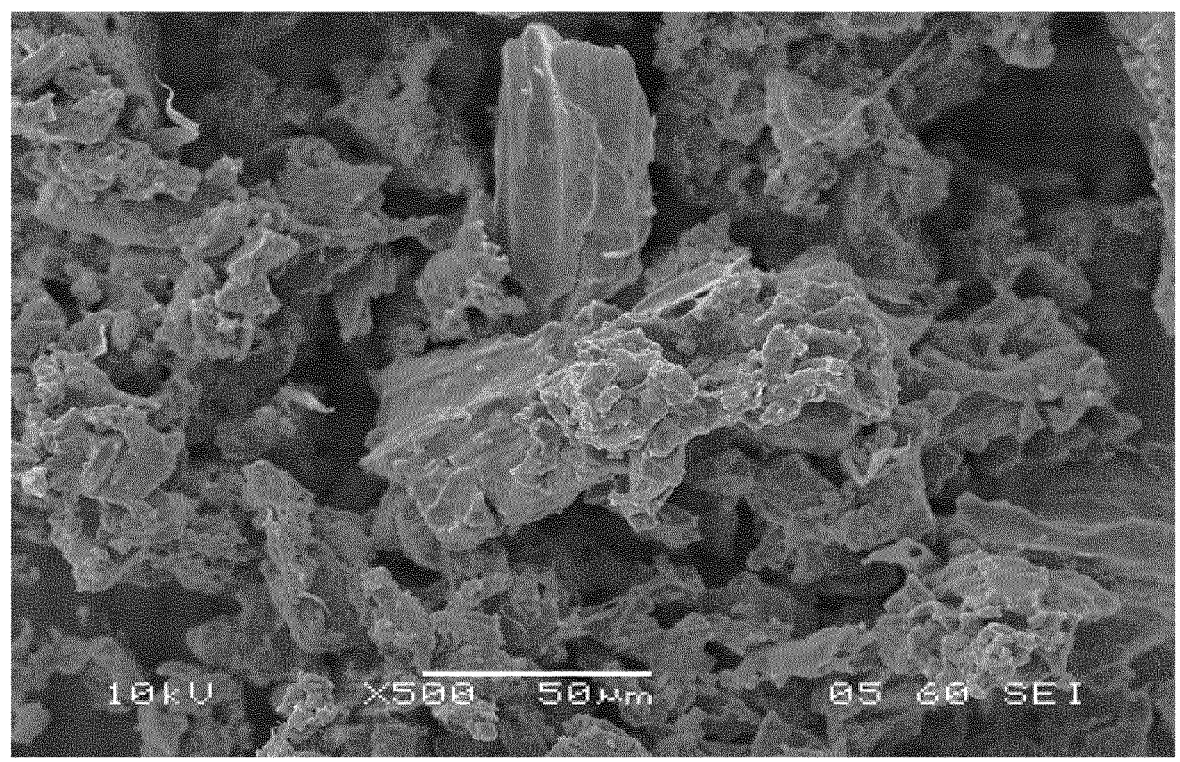

FIG: 2
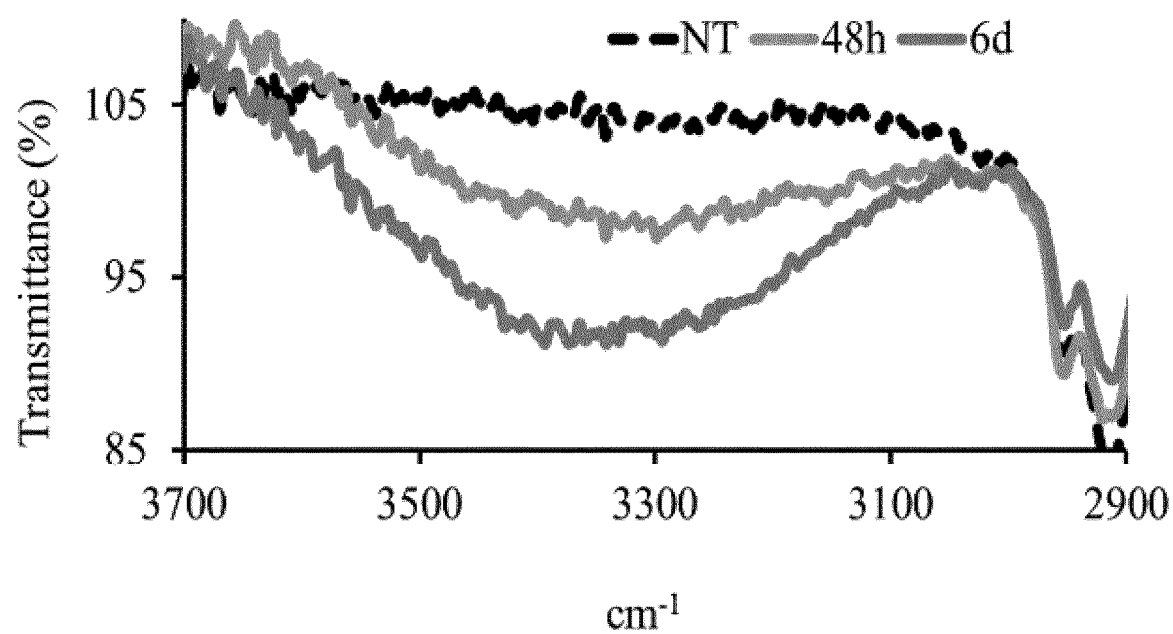

FIG: 3
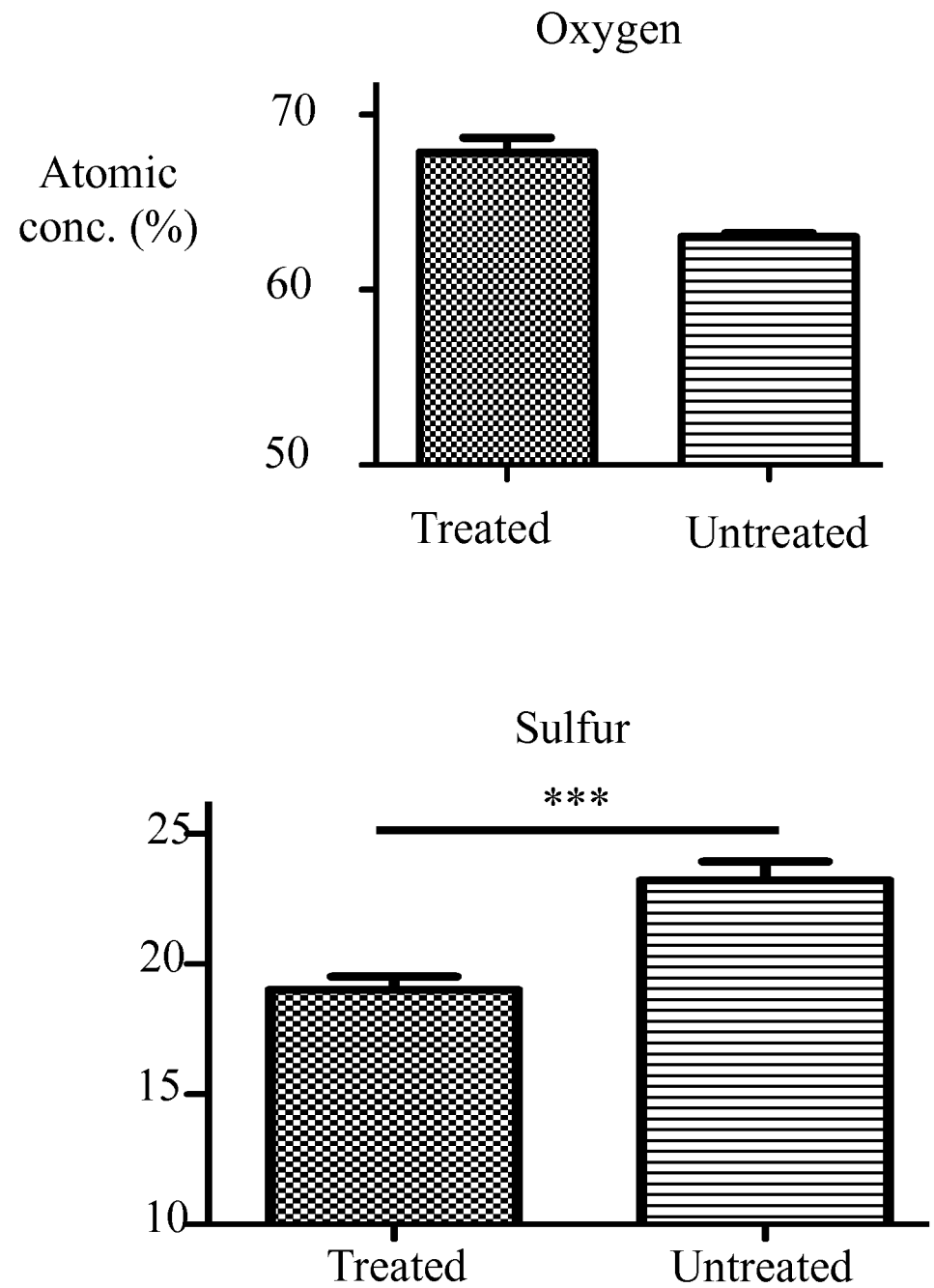

FIG: 4
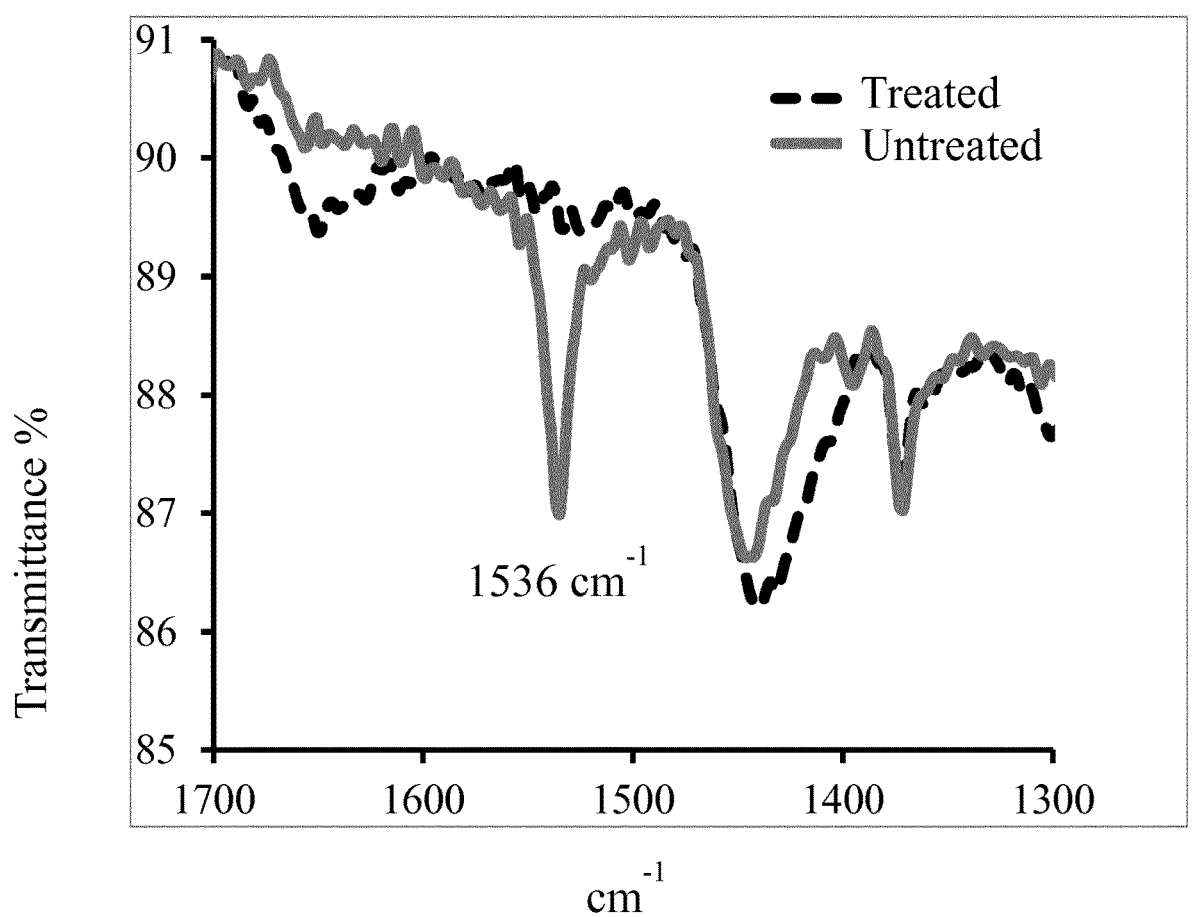

FIG: 5
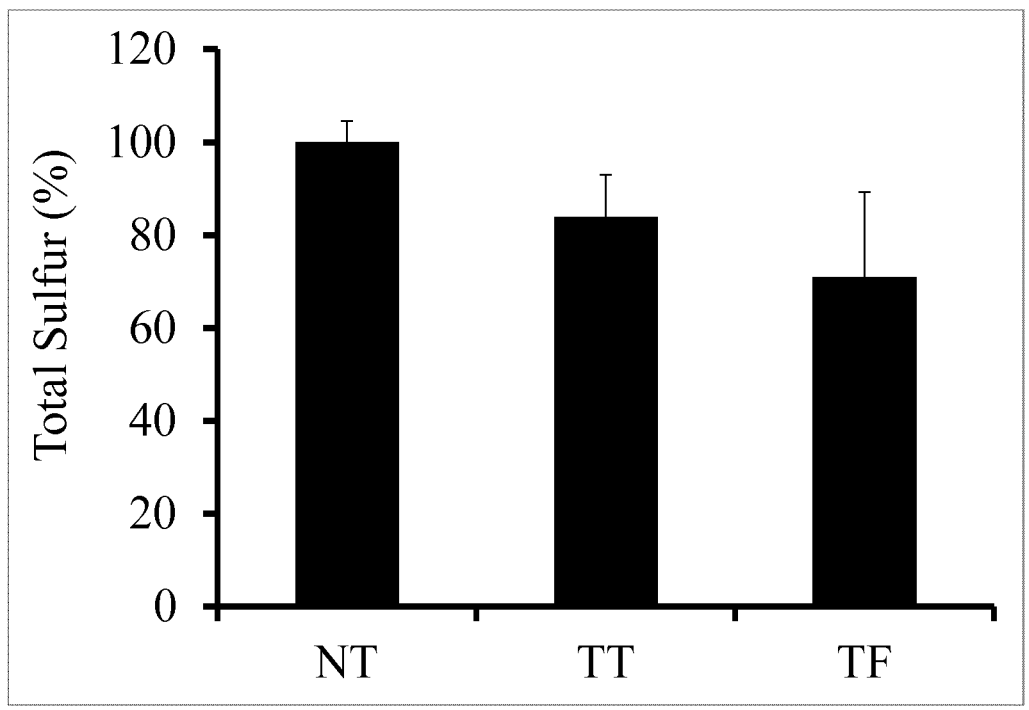
FIG: 6
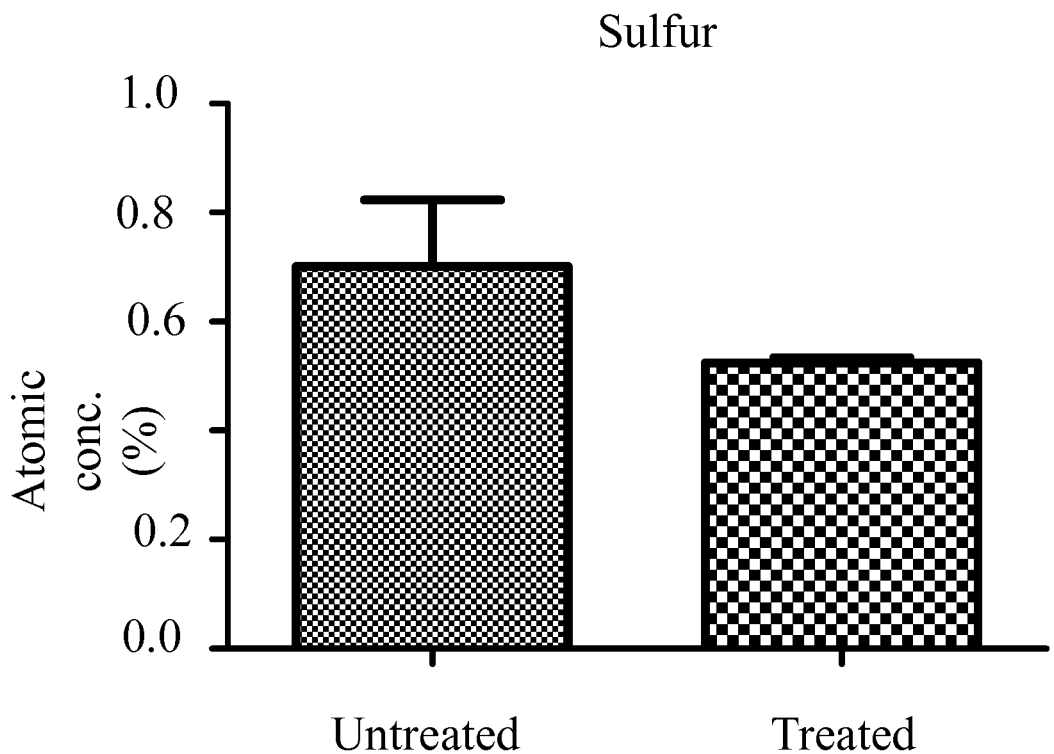

PROCESS FOR BACTERIALLY DEVULCANIZING SULPHUR-VULCANIZED RUBBER PARTICLES

FIELD OF THE INVENTION

The invention relates to a new *Acidithiobacillus ferrooxidans* strain as well as a process for bacterially devulcanizing sulphur-vulcanized rubber particles and devulcanized rubber particles obtainable by said process.

BACKGROUND OF THE INVENTION

Processes are known for microbial and enzymatic activation of powdered rubber and rubber granulates.

EP1620498 discloses a process for surface activation and/or devulcanisation of sulphur-vulcanised rubber particles. In order to break the sulphur bridges and to reduce the sulphur, the rubber particles are treated in a biotechnological manner in a medium with mesophilic anaerobic and/or mesophilic optionally anaerobic and/or mesophilic microaerophilic bacteria and/or with one or more enzyme systems of such bacteria.

EP0493732 discloses a method for reprocessing scrap rubber, which produces reclaimed rubber from comminuted scrap rubber after devulcanization, in a biotechnology-type of process, by holding the comminuted scrap rubber in a bacterial suspension of chemolithotrophic microorganisms with a supply of air, until sulphur as elementary sulphur and/or sulphuric acid is separated from the remaining replasticized reclaimed rubber. This biotechnological reprocessing obtains reclaimed rubber and sulphur in a simplified manner which products can be reused.

DE19728036A discloses a process for surface activation and modification of sulphur cross-linked rubber particles by biotechnical treatment in a suspension of the rubber particles, water and biologically active material for breaking the polysulphidic sulphur bridges and for oxidising the sulphur, by which the treatment is limited to the particle surface and reactive groups in the form of hydroxyl groups, epoxy groups and carboxyl groups are formed over a period of time, the biotechnical treatment being terminated when the concentration of reactive functional groups reaches a maximum.

U.S. Pat. No. 5,597,851 discloses a process which consists, on the one hand, in that thermophilic optionally chemolithotrophic *Sulfolobus acidocaldarius* is primarily used as a sulphur oxidizing microorganism and, on the other hand, the treatment of the rubber particles is carried out merely with the enzyme system of this microorganism. The rubber particles themselves are not in direct contact with the microorganisms.

Another process is disclosed in DE19728036 in which by biotechnological treatment of vulcanized rubber particles by means of defined reaction times/duration of oxidation, specific reactive functional groups in the form of hydroxyl groups, epoxy groups and carboxyl groups are produced on the particle surface. As a result, it is possible to vulcanize the activated powdered rubber and rubber granulates with different plastics, bitumens and other polymers. Bacteria of the *Thiobacillus* genus are also used for the microbial oxidation.

Romine A. Romine et al. «Rubbercycle: a bioprocess for surface modification of waste tyre rubber» Polymer degradation and stability 59 (1998) 353-358 discloses a screening of four microorganisms for ground tyre rubber (GTR) devulcanization. The tested microorganism are *Thiobacillus ferrooxidans, Thiobacillus thiooxidans, Rhodococcus rhodochrous, Sulfolobus acidocaldarius* and an unidentified bacterium ATCC #39327. The assessment of devulcanization was done by determining the concentration of sulphate in solution by ion chromatography and by material analyses techniques (FTIR with absorbance at 1032 cm-1 and XANES). The authors found oxidized sulphur species on the surface of GTR after 2-3 days of treatment and they determine that the bio-devulcanization process is complete after 7 days. Finally, they conclude that "*Thiobacillus* culture was not as effective as *S. acidocaldarius*". Globally, the authors only used one medium which is a standard growth medium also used for devulcanization. Further, Romine et al. did not consider a careful selection of the bacterial species to be used, the importance of a bacterial growth step before the devulcanization treatment and an adapted growth medium containing sulphur sources like sodium thiosulfate or tetrathionate and iron. This results in a devulcanization process presenting a low productivity which takes several days and which cannot be used at an industrial level Yuanhu Li et al. "Microbial desulfurization of ground tire rubber by *Thiobacillus ferrooxidans*" Polymer Degradation and Stability Vol. 96, No. 9, Pg 1662-1668 (2011) presents an approach for ground tire rubber (GTR) devulcanization using *T. ferrooxidans*. In particular, material analysis techniques for proving the devulcanization (FTIR and XPS) are used. However, there are major drawbacks with this approach due to the high chemical toxicity initially present in the GTR which results in biomass decrease after rubber addition on bacteria cultures. Consequently, only a limited amount of GTR may be treated and the devulcanization only takes place after 30 days of treatment. Thus there is a need to scale-up the devulcanization process of GTR or sulphur-vulcanized rubber particles so as to improve the process at an industrial level. Furthermore, delaying the vulcanization may also be of interest.

BRIEF DESCRIPTION OF THE INVENTION

One of the objects of the present invention is to provide an *Acidithiobacillus ferrooxidans* strain deposited under deposit number DSM 32046 on May 13, 2015, at the Leibniz Institute, DSMZ-German Collection of Microorganisms and Cell Cultures, Inhoffenstr 7B. D-38124 Braunschweig, Germany.

Another object of the present invention is to provide a process for aerobic bacterial devulcanization of sulphur-vulcanized rubber particles having a size of 10-2000 micron and wherein said sulphur-vulcanized rubber particles are obtainable by spraying rubber-containing articles with water under pressure and drying said resulting sulphur-vulcanized rubber particles to an initial water content of 0.01 to 20% by weight, the process comprising:

a) providing aerobic chemolithotrophic bacteria selected among the group consisting of the species *Acidithiobacillus thiooxidans, Acidithiobacillus ferrooxidans, Thiobacillus thioparus, Thiobacillus thiophilus* or a mixture thereof; in a medium for bacterial growth comprising an aqueous solution containing inorganic salts and an energy source for promoting bacterial devulcanization selected among the group comprising $Na_2SO_3$, $FeSO_4$, $FeCl_3$ and $Na_2S_4O_6$ or their mixtures;

b) adding said sulphur-vulcanized rubber particles to a treatment medium for devulcanization supplemented with said medium for bacterial growth containing said aerobic chemolithotrophic bacteria, wherein said treatment medium for devulcanization is depleted in any energy source for promoting bacterial devulcanization;

c) keeping said sulphur-vulcanized rubber particles into said treatment medium for devulcanization for a period comprised between 24 hours and 15 days; and
d) collecting and drying the resulting devulcanized rubber particles.

A further object of the invention is to provide devulcanized rubber particles obtainable by the process of the invention and characterized in that the obtained devulcanized rubber particles are chemically modified and contain sulfoxides and/or sulphur trioxides and/or methyl-assisted conjugated double-bonds and/or hydroxyl-groups and/or carboxyl-groups and/or epoxy groups on the surface of said devulcanized rubber particles.

Other objects and advantages of the invention will become apparent to those skilled in the art from a review of the ensuing detailed description, which proceeds with reference to the following illustrative drawings, and the attendant claims.

BRIEF DESCRIPTION OF THE FIGURES

FIG. 1: shows SEM images of rubber particles obtained by spraying car tyres with water under high pressure. Left: 150× magnification; right: 500× magnification.

FIG. 2: illustrates the FTIR analysis of tyres rubber powder treated with *A. ferrooxidans* strain DSM 32046. Peak at 3300 cm$^{-1}$: hydroxyl groups. NT: untreated; 48 h: treatment for 48 h, 6 d: treatment for 6 day FIG. 3: shows the EDX analysis of NR treated for 48 h with *A. ferrooxidans* strain DSM 32046. Untreated and treated values were compared by a Student t-test. ***$p<0.001$ FIG. 4: illustrates the FTIR analysis of tyres rubber powder treated with *A. ferrooxidans* strain DSM 32046. Peak at 1536 cm$^{-1}$: methyl-assisted conjugated double-bonds.

FIG. 5: shows the analysis of sulphur content on rubber particles by by combustion ionic chromatography. NT: untreated (100%), TT: treatment with *A. thiooxidans*, TF: treatment with *A. ferrooxidans*.

FIG. 6: Surface Sulphur quantification by SEM/EDX analysis of EPDM treated with *A. ferrooxidans* strain DSM 32046.

DETAILED DESCRIPTION OF THE INVENTION

Although methods and materials similar or equivalent to those described herein can be used in the practice or testing of the present invention, suitable methods and materials are described below. All publications, patent applications, patents, and other references mentioned herein are incorporated by reference in their entirety. The publications and applications discussed herein are provided solely for their disclosure prior to the filing date of the present application. Nothing herein is to be construed as an admission that the present invention is not entitled to antedate such publication by virtue of prior invention. In addition, the materials, methods, and examples are illustrative only and are not intended to be limiting.

In the case of conflict, the present specification, including definitions, will control. Unless defined otherwise, all technical and scientific terms used herein have the same meaning as is commonly understood by one of skill in art to which the subject matter herein belongs. As used herein, the following definitions are supplied in order to facilitate the understanding of the present invention.

Rubber is the main raw material used in manufacturing tires, and both natural and synthetic rubber are used. Natural rubber is found as a milky liquid in the bark of the rubber tree, *Hevea Brasiliensis*. To produce the raw rubber used in tire manufacturing, the liquid latex is mixed with acids that cause the rubber to solidify. Presses squeeze out excess water and form the rubber into sheets, and then the sheets are dried in tall smokehouses, pressed into enormous bales, and shipped to tire factories around the world. Synthetic rubber is produced from the polymers found in crude oil.

The other primary ingredient in tire rubber is carbon black. Carbon black is a fine, soft powder created when crude oil or natural gas is burned with a limited amount of oxygen, causing incomplete combustion and creating a large amount of fine soot.

Sulphur and other chemicals are also used in tires. Specific chemicals, when mixed with rubber and then heated, produce specific tire characteristics such as high friction (but low mileage) for a racing tire or high mileage (but lower friction) for a passenger car tire. Some chemicals keep the rubber flexible while it is being shaped into a tire while other chemicals protect the rubber from the ultraviolet radiation in sunshine.

In total, over 200 raw materials go into tire composition. Researchers draw on this extensive array to combine tire components, each of which has a role to play, depending on the type of tire produced. The rubber compounds are made up of elastomers, reinforcing fillers, plasticizers and others chemicals elements.

The term "comprise" is generally used in the sense of include, that is to say permitting the presence of one or more features or components.

As used in the specification and claims, the singular forms "a", "an" and "the" include plural references unless the context clearly dictates otherwise.

ATR-FTIR is the abbreviation for Fourier Transform Infrared Spectroscopy coupled to Attenuated Total reflection module.

Chemolithotrophic bacteria are bacteria able to deriving energy from the oxidation of inorganic compounds of iron, nitrogen, sulphur, or hydrogen.

An aerobic bacteria is an organism that can survive and grow in an oxygenated environment.

Devulcanization is the modification of the surface chemistry of rubber particles by bacteria, which cause the reduction of sulphur content on the rubber matrix and the addition of chemical groups, such as hydroxyl groups. Devulcanization occurs when rubber particles are added in the devulcanization media supplemented by the bacteria.

Devulcanized-rubber particles are rubber particles that were subjected to devulcanization.

A dienophile is the olefinic or acetylenic component that is seeking a diene in the Diels-Alder reaction.

EPDM represents ethylene-propylene diene monomer rubber

NR is the abbreviation of natural rubber. Milky, white latex, containing rubber globules, is obtained by making an incision into the bark of rubber trees, the cultivation of which requires specific climatic conditions and rainfall. Rubber tree plantations are mainly located in Southeast Asia (including Thailand, the world's largest producer and Indonesia), Latin America and Africa. In compound formulations, natural rubber reduces internal heat generation in tires, whilst offering high mechanical resistance. It is used in many parts of the tire, mainly used for truck and earthmover tire tread.

SBR is the abbreviation of styrene butadiene rubber. 60% of rubber used in the tire industry is synthetic rubber, produced from petroleum-derived hydrocarbons, although natural rubber is still necessary for the remaining 40%. Synthetic elastomers deform under stress and return to their original shape when the stress is removed (hysteresis). This property is extremely valuable for the manufacture of high-grip tires. Synthetic rubber also provides other specific properties, most notably in the areas of longevity and rolling resistance. It's mainly used for passenger car and motorcycle tire as it gives them good grip performances.

SEM/EDX represents the abbreviation of scanning electron microscope coupled with an energy dispersive X-ray analysis system.

The present invention concerns an *Acidithiobacillus ferrooxidans* strain deposited under deposit number DSM 32046.

Another object of the invention is to provide a process for aerobic bacterial devulcanization of sulphur-vulcanized rubber particles having a size of 10-2000 micron and wherein said sulphur-vulcanized rubber particles are obtainable or obtained by spraying rubber-containing articles with water under pressure and drying said resulting sulphur-vulcanized rubber particles to an initial water content of 0.01 to 20% by weight, the process comprising:
  a) providing aerobic chemolithotrophic bacteria selected among the group consisting of the species *Acidithiobacillus thiooxidans, Acidithiobacillus ferrooxidans, Thiobacillus thioparus, Thiobacillus thiophilus* or a mixture thereof; in a medium for bacterial growth comprising an aqueous solution containing inorganic salts and an energy source for promoting bacterial devulcanization selected among the group comprising Na2SO3, FeSO4, FeCl3 and Na2S4O6 or their mixtures;
  b) adding said sulphur-vulcanized rubber particles to a treatment medium for devulcanization supplemented with said medium for bacterial growth containing said aerobic chemolithotrophic bacteria, wherein said treatment medium for devulcanization is depleted in any energy source for promoting bacterial devulcanization;
  c) keeping said sulphur-vulcanized rubber particles into said treatment medium for devulcanization for a period comprised between 24 hours and 15 days; and
  d) collecting and drying the resulting devulcanized rubber particles.

One important difference between the approach described in Yuanhu Li et al. and the present invention is the choice of the pulverization/grounding techniques to obtain GTR. While the most popular approach to recycling tires is through mechanical grinding Applicants have chosen a technology that utilizes high pressure water to completely break down scrap tires. The high pressure or ultra-high pressure water jet milling technology can be considered as a new direction for fine milling of elastomers, such as rubber and similar elastic materials. Instead of conventional shredding and mechanical grinding of tyres, this technology applies only high pressure water jet (i.e. as described in U.S. Pat. No. 5,115,983 A; D&R Recycling, Inc.) for extraction and simultaneous milling of rubber (elastic) parts so as to obtain a fine rubber powder.

In particular, the pulverization technique of the present invention is based on high-pressure water or water-jet combined with an optimized culture media allowing a reduction of the toxic chemicals present in the GTR. Advantageously, Applicants are able to work with increased concentration of GRT (preferably 20% instead of 5% as presented by Li et al.) and without observing any biomass decrease after rubber addition on bacterial cultures. Further the present invention is based on a specific choice of bacterial species and of growth medium using a combination between iron and sulphur-bonds containing compounds, such as thiosulfate and tetrathionate, increasing the ability of bacteria to use disulphide bonds in GTR as source of energy. Surprisingly, the devulcanization process of the invention already takes place after 48 h of treatment instead of 30 days as described by Li et al.

Preferably the rubber-containing articles are selected from tires or tires segments, tire treads, shoe-soles, conveyor belts. The rubber-containing articles also include but are not limited to pneumatic tires, rubber boots, rubber clothing, wet-suits, dry-suits, bumpers, road fenders, marine fenders, rubber dampers, pads for tank tracks, rubber crawler tracks, machine anti-vibration pads, protective rail car liners, noise insulation pads, flooring tiles, rail dampers, boat trailer pads, wind-shield wiper blades, extruded profiles, injection moulding cores, mud flaps. Pneumatic tires are used on many types of vehicles, including cars, bicycles, motorcycles, trucks, heavy equipment and aircraft. Solid rubber (or other polymer) tires are used in various non-automotive applications, such as some casters, carts, lawnmowers and wheelbarrows. Heavy duty tires are also referred to as Truck/Bus tires.

The sulphur-vulcanized rubber particles to be devulcanized are advantageously obtained by spraying rubber-containing articles such as tires or tire segments with water under high pressure and drying the resulting particles.

According to one embodiment of the invention, the volume of the medium for bacterial growth containing said aerobic chemolithotrophic bacteria that is supplemented to the treatment medium for devulcanization is comprised between 10 to 80%.

In a preferred embodiment, the sulphur-vulcanized rubber particles of Step b) are added at a concentration between 1 and 35% by weight.

In accordance with the process of the invention, the aerobic chemolithotrophic bacteria of Step a) are employed as a pure strain or in a community.

Advantageously, the medium for bacterial growth of Step a) and the treatment medium for devulcanization of Step b) are agitated. Preferably, the agitation comprises vertical or horizontal helically agitated mixing in a range of 10 to 300 revolutions per minute (rpm) and/or orbitally shaking in a range of 10 to 500 rpm and/or air insufflation in a range of 0.01 to 20 L/min.

The medium for bacteria culture and growth contains: $Na_2SO_3$, $FeSO_4$, $FeCl_3$ and $Na_2S_4O_6$ or their mixtures
  a. $Na_2SO_3$ and/or $FeSO_4$ in a concentration comprised between 0.05 to 4.0 g/L and/or
  b. $FeCl_3$ and/or $Na_2S_4O_6$ in a concentration comprised between 0.05 to 10.0 g/L.

In another preferred embodiment, the treatment medium for devulcanization of Step b) further contains dienophiles and organic acids. Preferably, the organic acids are selected among the group of maleic acid, pyruvic acid, benzoic acid, salicylic acid and or their mixtures. Usually, the dienophiles are selected among the group consisting of maleic anhydride, 2-oxopropanal or their mixtures. In particular, the medium for bacteria culture and growth may comprise salicylic acid in a concentration comprised between 0, preferably 0.01, to 0.5 g/L and/or benzoic acid in a concentration comprised between 0, preferably 0.01, to 0.5 g/L and/or pyruvic acid in a concentration comprised between 0, preferably 0.01, to 0.5 g/L and/or maleic acid in a concentration comprised between 0, preferably 0.01, to 0.5 g/L According to another embodiment of the invention, the medium for bacterial growth further comprises at least one optional further constituent selected from: MnSO4; Leucine; Thymol; Salicylic acid or their mixtures.

The pH between 1.0 to 7.0, preferably between 1.5 to 6.5, of the medium for bacteria growth can be regulated by using 1M to 10M HCl, 60% to 98% $H_2SO_4$, 1M to 10M NaOH and 1M to 2M $K_2CO_3$.

Consumption of the energy source for bacteria growth is monitored by assessing $Fe^{2+}$ and/or $Fe^{3+}$ concentration by measuring the absorbance of the media at 220-250 nm ($Fe^{2+}$) and/or 280-340 nm ($Fe^{3+}$) and/or by analysis with inductively coupled plasma mass spectrometry (ICP) and/or with Atomic Absorption Spectroscopy (AAS), wherein $Na2S_2O_3$ utilization is determined by methylene blue discoloration and/or ion chromatography, and wherein sulphur oxidation is determined by measuring the oxygen consumption by means of a respirometer.

In a preferred embodiment of the invention, the aerobic chemolithotrophic bacteria of Step a) is the *Acidithiobacillus ferrooxidans* strain deposited under deposit number DSM 32046 employed as a pure strain or in a community.

The necessity to culture bacteria separately as a stock of living microorganisms for devulcanization is fundamental for an efficient industrialization of the process.

The presence of contaminations in the rubber powder represents an obstacle for an efficient devulcanization, since the source of contaminations (fungi or other bacteria) may interfere with the growth of the selected bacteria, may degrade the rubber particles and may interfere with the chemical and enzymatic reactions involved in the devulcanization.

Optionally, rubber particles are sterilized before and/or after the devulcanization in order to avoid contaminations from bacteria and other microorganisms by γ-sterilization or steam sterilization or chemical sterilization based on ethylene oxide or nitrogen dioxide or ozone.

The invention will be more clearly understood, from the following description of a preferred embodiment, which is given by way of example only.

In a preferred embodiment, the invention provides a process for bacterially devulcanizing sulphur-vulcanized rubber particles having a size of 10-2000 micron, preferably of 10-900 micron, and more preferably a size of 150-600 micron, and an initial moisture content of 0.01 to 20%, preferably of 0.01 to 5% by weight and more preferably of 0.1 to 4%. The sulphur-vulcanized rubber particles to be treated can come from many sources. For instance, the sulphur-vulcanized rubber particles can be obtained by spraying tires or tire segments with water under high pressure and drying the resulting particles. In this case, the sulphur-vulcanized rubber particles to be devulcanized may be subjected to a preliminary drying treatment to reach the specified initial moisture content. In a less preferred variant, sulphur-vulcanized rubber particles can come from a comminution process which does not require a drying treatment.

In said preferred embodiment, rubber particles are sterilized by γ-sterilization steam sterilization before the devulcanization in order to avoid contaminations from bacteria and other microorganisms.

In said preferred embodiment, bacteria are selected from aerobic chemolithotrophic organisms. In a first embodiment, *Acidithiobacillus thiooxidans* represent 30% of the community and *Acidithiobacillus ferrooxidans* represent 30% of the community and *Thiobacillus* thioparus represent 30% of the community and *Thiobacillus thiophilus* represent 10% of the community.

The community of bacteria are subject to a culture process to grow the bacteria, in a bacterial growth medium comprising an aqueous solution containing inorganic salts at a pH from 0.5 to 7, preferably from 0.5 to 4.5, and a temperature of 20 to 35° C., preferably from 20 to 30° C., said culture medium further comprising an energy source for promoting bacteria growth, selected from $Na_2SO_3$ and/or $FeSO_4$, and/or $FeCl_3$ and/or $Na_2S_4O_6$ and/or their mixtures. The pH of the medium for bacteria growth may be regulated by using 1M to 10M HCl, 60% to 98% $H_2SO_4$, 1M to 10M NaOH and/or 1M to 2M $K_2CO_3$.

The growth medium can be agitated by different ways. Agitation can be vertical or horizontal helically agitated mixing in a range of 10 to 300 revolutions per minute (rpm), preferably 30 to 100 120 rpm, or orbitally shaking in a range of 10 to 500 rpm, preferably 50 to 200 rpm, or air insufflation in a range of 0.01 to 20 L/mn.

Consumption of the energy source for bacteria growth is monitored by measuring the absorbance of the media at 220-250 nm ($Fe^{2+}$) and/or 280-340 nm ($Fe^{3+}$) or by measuring $Fe^{2+}$ to $Fe^{3+}$ oxidation colorimetrically or 230-260 nm ($Na_2S_2O_3$), wherein $Na_2S_2O_3$ utilization is determined by iodine titration methylene blue decoloration, and wherein sulphur oxidation is determined by measuring the oxygen consumption by means of a respirometer.

The rubber particles are then subject to a sulphur devulcanization treatment in a treatment medium comprising the bacteria and containing a concentration of rubber particles between 1 and 35% by weight. During devulcanization the medium is preferably at a pH from 0.5 to 4.5 and at a temperature of 20 to 30° C.

In said preferred embodiment, the treatment medium comprising the bacteria and containing a concentration of rubber particles between 1 and 35% by weight further contains $MgSO_4$ in a concentration comprised between 0.05 to 4.0 g/L, preferably between 0.05 to 3.0 g/L, and $K_2HPO_4$ in a concentration comprised between 0.05 to 10.0 g/L, preferably between 0.05 and 3.5 g/L, and $(NH_4)_2SO_4$ in a concentration comprised between 0.05 to 10.0 g/L, preferably between 2.0 to 8.0 g/L. This medium may comprise at least one optional further constituent selected from:
a. KCl in a concentration comprised between 0.1 to 2 g/L, and/or
b. $Ca(NO_3)_2$ in a concentration comprised between 0.1 to 0.5 g/L, and/or
c. Chemicals selected from thymol in a concentration comprised between 0.01 to 0.5 g/L and/or salicylic acid in a concentration comprised between 0.01 to 0.5 g/L and/or pyruvic acid in a concentration comprised between 0.01 to 0.5 g/L and/or maleic acid in a concentration comprised between 0.01 to 0.5 g/L.

The devulcanization treatment can last for 24 hours to 12 days.

After the end of the process, the resulting devulcanized rubber particles are humid and are dried to a moisture content of 0.01 to 15% by weight.

In an additional step, rubber particles are sterilized after the devulcanization in order to avoid contaminations from bacteria and other microorganisms by γ-sterilization heating or steam sterilization.

It is another object of the invention to provide for a devulcanized rubber particles obtainable (or obtained) by the above-identified process and wherein the obtained devulcanized rubber particles are chemically modified and contain sulfoxides and/or sulphur trioxides and/or methyl-assisted conjugated double-bonds and/or hydroxyl-groups and/or carboxyl-groups and/or epoxy groups on the surface of said devulcanized rubber particles.

Further the devulcanized rubber particles of the invention are defined by the presence of free organic matter in a concentration between 0.1% to 0.5% by weight, the reduction of over 80% of the concentration of volatile compounds such as cyclo hexanone, cyclopropane and ethanol in a NR/SBR mixture (car tires), a reduction of the concentration of Methyl isobutyl ketone (MIBK) of at least 50% (in car and truck tires), an increased wettability assessed by measuring the reduction of water contact angle in a range between 75% to 95% as well as an increase of water retain in a range between 75% to 150%.

Water retain was assessed by measuring the percentage of distilled water retained in a defined amount of rubber particles.

Water contact angle was assessed by measuring the water contact angle of a drop of water on the surface of a rubber compound. A horizontal picture is taken for each drop and the contact angle is measured on the picture.

Further it was observed (see example 2) a reduction of the concentration of Methyl isobutyl ketone (MIBK) (used as solvents in the tires) in the range of 50% to 80% in SBR and NR (in car and truck tires), as well as a reduction of over 80% of the concentration of volatile compounds such as cyclo hexanone, cyclopropane and ethanol in a NR/SBR mixture (car tires). In particular, volatile organic compounds were identified and quantified by Headspace Gas Chromatography Mass Spectrometry (HS-GC-MS).

Those skilled in the art will appreciate that the invention described herein is susceptible to variations and modifications other than those specifically described. It is to be understood that the invention includes all such variations and modifications without departing from the spirit or essential characteristics thereof. The invention also includes all of the steps, features, compositions and compounds referred to or indicated in this specification, individually or collectively, and any and all combinations or any two or more of said steps or features. The present disclosure is therefore to be considered as in all aspects illustrated and not restrictive, the scope of the invention being indicated by the appended Claims, and all changes which come within the meaning and range of equivalency are intended to be embraced therein.

Various references are cited throughout this specification, each of which is incorporated herein by reference in its entirety.

The foregoing description will be more fully understood with reference to the following Examples. Such Examples, are, however, exemplary of methods of practising the present invention and are not intended to limit the scope of the invention.

EXAMPLES

Rubber particles are obtained by spraying tyres with water at a rate of between 1 and 4 meters per minute, with water under high-pressure in the range of 800 to 3000 bars, and then dried. These particles are characterized by a high surface area and an irregular shape (FIG. 1). The particles thus obtained have a size-distribution comprised between 2000 and 50 micrometers.

A general protocol for the treatment of rubber particles with selected bacteria is described below. In general, bacteria are maintained in culture with inorganic salt and energetic substrate for promoting their expansion. For the treatment of the rubber powder, the aqueous media is depleted of the energetic sources in order to promote targeting of sulphured compound present in the rubber. Due to that, bacteria directly use sulphur compound from the rubber particles as a source of energy and this leads to devulcanization of the rubber.

Example 1

*Acidithiobacillus ferrooxidans* strain DSM 32046 are maintained in culture in an aqueous growth media containing 0.5 g/L $FeSO_4$, 0.4 g/L $MgSO_4$, 0.6 g/L $(NH_4)2SO4$, 0.4 g/L $K_2HPO4$, 0.3 g/L K2S4O6. The pH is adjusted with H2SO4 at 2.20. Bacteria are grown in 500 L bioreactors.

When the bacteria count reaches $1\times106$ bacteria/mL, 750 L of the bacteria medium from the grown cultures are diluted with devulcanization medium in a ratio of 1:6 into the devulcanization bioreactor, to reach a final volume of 3,000 L. The devulcanization media is composed by 0.6 g/L MgSO4, 2 g/L (NH4)2SO4, 0.2 g/L KH2PO4, 0.5 g/L K2HPO4.

Then rubber particles composed by NR are added into the devulcanization bioreactor in a concentration of 20% weight/volume (600 kg for 3,000 L). The mixture of rubber particles and bacteria is maintained under agitation at 100 rpm at a temperature of 30° C. for 48 hours or 6 days.

After treatment, rubber particles are separated from the aqueous medium by passing the mixture through a drainer (commercially available), then dried at 120° C. in an industrial commercially available installation, to obtain a rubber powder with 1.0+0.3% moisture.

Treated rubber particles are analysed by ATR-FTIR and by SEM/EDX. The ATR-FTIR analysis shows the appearance of hydroxyl groups on the surface of the rubber particles (see FIG. 2, broad peak at 3,300 cm-1). The intensity of the peak, which is attributable to the quantity of hydroxyl groups, is time depended and increases after 6 days of treatment (FIG. 2). The SEM/EDX analysis of the rubber particles after 48 h of treatment showed a decrease of sulphur on the surface of the particles and an increase of oxygen, confirming the presence of hydroxyl groups on the surface (FIG. 3). Together, these results show that the selected strain of *A. ferrooxidans* is particularly effective in performing the devulcanization of the rubber particles and that this effect is treatment time-dependent.

Moreover, the rubber powder before treatment presents some methyl-assisted conjugated doubles bonds on the surface, which is visible by ATR-FTIR analysis (peak at 1536 cm-1, FIG. 4). These chemical structures decrease the mechanical properties of the rubber and the treatment with *A. ferrooxidans* in presence of salicylic acid allows the disappearing of these undesired structures (FIG. 4). This prove that the bacteria treatment according to the invention causes the modification of the surface chemistry of the rubber particles and advantageously increases the mechanical properties of the final product.

Example 2

Two strains of *thiobacilli*, the *A. ferrooxidans* strain DSM 32046 and one *Acidithiobacillus thiooxidans* strain, are grown separately in 15 L bioreactors.

The growth media for *A. ferrooxidans* strain is composed by 0.1 g/L FeSO4, 0.5 g/L MgSO4, 3 g/L (NH4)2SO4, 0.5 g/L K2HPO4, 2 g/L Na2S2O3 and 0.05 g/L salicylic acid. The pH is adjusted with H2SO4 at 4.5.

The growth medium for *A. thiooxidans* strain is composed by 0.05 g/L MnSO4, 0.5 g/L MgSO4, 3.0 g/L (NH4)2SO4, 2.0 g/L KH2PO4, 2.0 g/L Na2S2O3 and 0.05 g/L salicylic acid. The pH is adjusted with H2SO4 at 4.5.

When the bacteria count reaches 1×106 bacteria/mL, 10 L of the bacteria medium from each stock cultures are separately diluted with the devulcanization medium in a ratio of 1:3 into the two devulcanization bioreactors (one per strain), to reach a final volume of 30 L.

The devulcanization media for *A. ferrooxidans* strain is composed by 0.5 g/L MgSO4, 3.0 g/L (NH4)2SO4, 0.8 g/L KH2PO4, 1.0 g/L K2HPO4, 0.05 g/L salicylic acid and 0.01 g/L pyruvic acid.

The devulcanization media for *A. thiooxidans* strain is composed by 0.5 g/L MgSO4, 3.0 g/L (NH4)2SO4, 2.0 g/L KH2PO4, 1.0 g/L K2HPO4, 0.05 g/L salicylic acid and 0.01 g/L pyruvic acid.

Then the rubber particles composed by SBR/NR are added into the devulcanization bioreactors in a concentration of 20% weight/volume (6 kg for 30 L). The mixture of rubber particles and bacteria is maintained under agitation at 100 rpm at a temperature of 30° C. for 48 hours.

After treatment, the rubber particles are separated from the aqueous medium by passing the mixture through a drainer (commercially available), then dried at 55° C. in an industrial commercially available installation, to obtain a rubber powder with 1.5+0.2% moisture.

The total sulphur content of the treated particles is analysed by combustion ionic chromatography. A decrease of 16% and of 29% of the total sulphur content in the treated particles is observed after treatment with *A. thiooxidans* and *A. ferrooxidans*, respectively (FIG. 5). These results demonstrate that both species are able to reduce the sulphur content on the rubber particles, thus fully able to perform the devulcanization.

Moreover, the rubber powder before treatment presents some methyl-assisted conjugated doubles bonds on the surface, which is visible by ATR-FTIR analysis (peak at 1536 cm-1, FIG. 5). These chemical structure decrease the mechanical properties of the rubber and the treatment with *A. ferrooxidans* in the presence of salicylic acid allows the disappearing of these undesired structures (FIG. 5). This proves that the bacterial treatment causes the modification of the surface chemistry of the rubber particles and advantageously increases the mechanical properties of the final product.

Finally, the release of volatiles compounds on particles treated with *A. ferrooxidans* and untreated rubber particles was assessed by HS-GC-MS namely volatile organic compounds were identified and quantified by Headspace Gas Chromatography Mass Spectrometry (HS-GC-MS). Globally, a decrease of the volatiles concentration after treatment was measured. In particular, the concentration of methyl isobutyl ketone (MIBK) decreased by 70%, the concentration of cyclo hexanone decreased by 82%, the concentration of cyclopropane decreased by 84% and the concentration of ethanol decrease by 87%.

Example 3

The *A. ferrooxidans* strain DSM 32046 is grown as described in example 2.

When the bacteria count reaches 1×106 bacteria/mL, 10 L of the bacteria medium from the stock culture are diluted with the devulcanization medium (composition as described in example 2) in a ratio of 1:3 into the devulcanization bioreactor, to reach a final volume of 30 L.

Then rubber particles composed by EPDM are added into the devulcanization bioreactors in a concentration of 10% weight/volume (3 kg for 30 L). The mixture of rubber particles and bacteria is maintained under agitation at 100 rpm at a temperature of 30° C. for 48 hours. At the end of the treatment, the obtained particles are drained and dried as described in example 2, so as to obtain a rubber powder with ~1.5% moisture. Treated and untreated particles were analysed by MEB/EDX and it was shown a decrease of the content of sulphur on the surface of the particles after treatment, evidencing that *A. ferrooxidans* strain DSM 32046 is able to devulcanize several types of rubbers.

Example 4

Two strains of *thiobacilli*, one *Thiobacillus* thioparus and one *Thiobacillus thiophilus*, are grown separately in 15 L bioreactors.

The growth media of the *T. thioparus* is composed by 0.01 g/L MnSO4, 0.5 g/L MgSO4, 0.1 g/L (NH4)2SO4, 4.0 g/L KH2PO4, 2.0 g/L K2HPO4, 0.15 g/L FeCl3 and 5.0 g/L Na2S2O3. The pH is adjusted with H2SO4 at 6.5.

The growth media of the *T. thiophilus* is composed by 0.8 g/L NH4Cl, 1.0 g/L MgSO4, 0.1 g/L (NH4)2SO4, 2.0 g/L KH2PO4, 0.2 g/L K2HPO4, 0.8 g/L KNO3 and 5.0 g/L Na2S2O3. The pH is adjusted with H2SO4 at 6.5.

These strain are employed for NR devulcanization as described in example 2.

The devulcanization media for *T. thioparus* is composed by 0.8 g/L MgSO4, 0.25 g/L (NH4)2SO4, 4.0 g/L KH2PO4, 0.5 g/L K2HPO4 and 0.05 g/L FeCl3.

The growth media for *T. thiophilus* is composed by 0.8 g/L NH4Cl, 1.0 g/L MgSO4, 0.25 g/L (NH4)2SO4, 2.0 g/L KH2PO4, 0.5 g/L K2HPO4 and 1.0 g/L KNO3.

Preliminary results obtained by ATR-FTIR and SEM/EDX showed that these strains are fully effective in devulcanizing rubber particles under the process according to the present invention.

The invention claimed is:

1. A process for aerobic bacterial devulcanization of sulphur-vulcanized rubber particles; the process comprising:
  a) milling rubber-containing particles by spraying the rubber-containing particles with water under pressure and drying said resulting sulphur-vulcanized rubber particles having a size of 10-2000 micron to an initial water content of 0.01 to 20% by weight,
  b) providing aerobic chemolithotrophic bacteria selected from the group consisting of the species *Acidithiobacillus thiooxidans, Acidithiobacillus ferrooxidans* comprising the *Acidithiobacillus ferrooxidans* strain deposited under deposit number DSM 32046, *Thiobacillus* thioparus, *Thiobacillus* thiophilus, and a mixture thereof; in a medium for bacterial growth comprising an aqueous solution containing inorganic salts and an energy source for promoting bacterial devulcanization selected from the group consisting of Na2SO3, FeSO4, FeCl3 and Na2S4O6 and their mixtures;
  c) adding said sulphur-vulcanized rubber particles to a supplemented treatment medium comprising:
    a treatment medium for devulcanization that is depleted in any energy source for promoting bacterial devulcanization; and
    said medium for bacterial growth containing said aerobic chemolithotrophic bacteria;
  d) keeping said sulphur-vulcanized rubber particles in said supplemented treatment medium for a period comprised between 24 hours and 15 days; and e) collecting and drying the resulting devulcanized rubber particles.

2. The process for aerobic bacterial devulcanization according to claim 1, wherein the rubber-containing articles are selected from tires or tires segments, tire treads, shoe-soles, and conveyor belts.

3. The process for aerobic bacterial devulcanization of claim 1, wherein the volume of said medium for bacterial growth containing said aerobic chemolithotrophic bacteria comprised in the supplemented treatment medium is between 10 to 80%.

4. The process for aerobic bacterial devulcanization according to claim 1, wherein said sulphur-vulcanized rubber particles of Step c) are added at a concentration between 1 and 35% by weight.

5. The process for aerobic bacterial devulcanization according to claim 1, wherein said aerobic chemolithotrophic bacteria of Step b) are employed as a pure strain or in a community.

6. The process for aerobic bacterial devulcanization according to claim 1, wherein the medium for bacterial growth of Step b) and the treatment medium for devulcanization of Step c) are agitated.

7. The process for aerobic bacterial devulcanization according to claim 1, wherein the treatment medium for devulcanization of Step c) further contains dienophiles and organic acids.

8. The process for aerobic bacterial devulcanization of claim 7, wherein the organic acids are selected from the group consisting of maleic acid, pyruvic acid, benzoic acid, salicylic acid and their mixtures.

9. The process for aerobic bacterial devulcanization of claim 7, wherein the dienophiles are selected from the group consisting of maleic anhydride, 2-oxopropanal and their mixtures.

10. The process for aerobic bacterial devulcanization according to claim 1, wherein the medium for bacterial growth further comprises at least one optional further constituent selected from: $MnSO_4$, Leucine, Leucine, Salicylic acid and their mixtures.

11. The process for aerobic bacterial devulcanization according to claim 1, wherein consumption of the energy source for bacteria growth is monitored by assessing $Fe^{2+}$ and/or $Fe^{3+}$ concentration by measuring the absorbance of the media at 220-250 nm ($Fe^{2+}$) and/or 280-340 nm ($Fe^{3+}$) and/or by analysis with inductively coupled plasma mass spectrometry (ICP) and/or with Atomic Absorption Spectroscopy (AAS), wherein $Na_2S_2O_3$ utilization is determined by methylene blue discoloration and/or ion chromatography, and wherein sulphur oxidation is determined by measuring the oxygen consumption by means of a respirometer.

12. The process for aerobic bacterial devulcanization according to claim 1, wherein said *Acidithiobacillus ferrooxidans* strain deposited under deposit number DSM 32046 of Step b) is employed as a pure strain or in a community.

13. The process for aerobic bacterial devulcanization according to claim 1, wherein the water is sprayed in Step a) under pressure in the range of 800 to 3,000 bars.

14. The process for aerobic bacterial devulcanization according to claim 1, wherein the water is sprayed in Step a) at a rate of between 1 and 4 meters per minute.

* * * * *